July 18, 1967 E. D. HUDSON Plant Pat. 2,754
AZALEA PLANT
Filed May 23, 1966
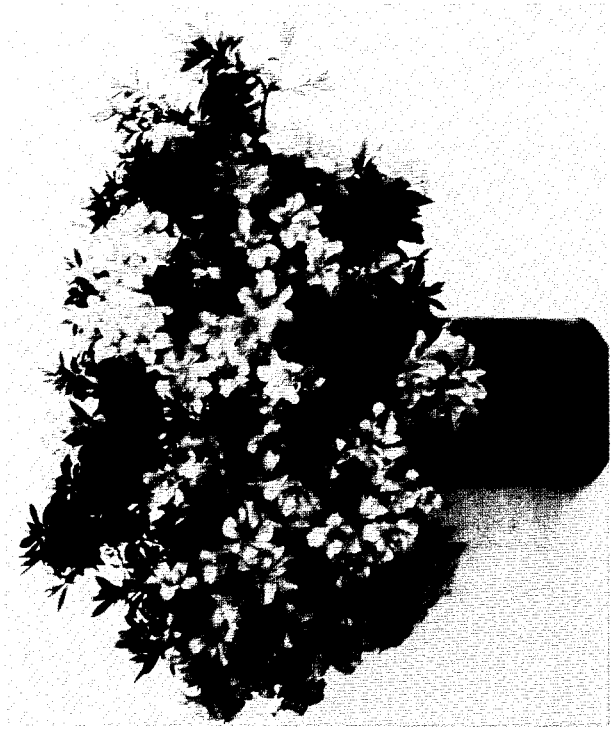
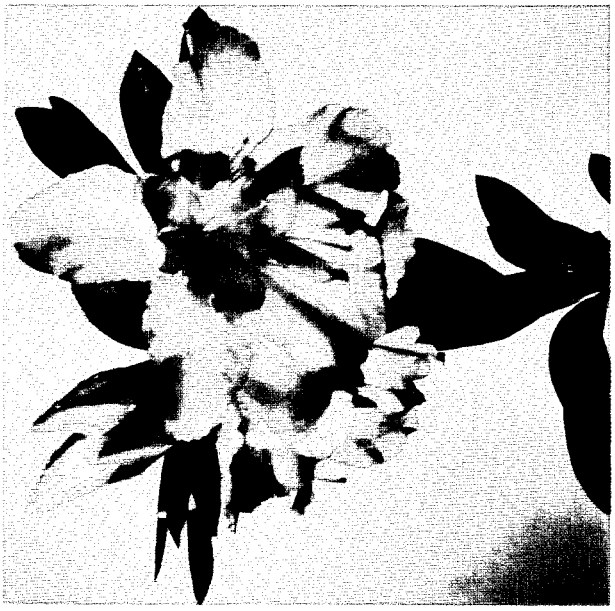
INVENTOR.
EARL D. HUDSON,
By Edmond F. Shanahan.
ATTORNEY.

United States Patent Office

Plant Pat. 2,754
Patented July 18, 1967

2,754
AZALEA PLANT

Earl D. Hudson, Hemet, Calif., assignor to Monrovia Nursery Co., Azusa, Calif., a corporation of California Filed May 23, 1966, Ser. No. 552,355
1 Claim. (Cl. Plt.—56)

The present invention relates to a new and distinct variety of azalea plant.

The plant is characterized as to novelty by the unique coloring of its flowers, both in shade and in pattern, as illustrated and described herein; by its abundant rich green foliage; by its ability to grow and flower in full sun or light shade; and by its compact, densely branched habit of growth.

I discovered the original plant as a seedling originating in December 1959, and first flowering in December 1961. It will not come true from seeds; however, it has been propagated by grafting and cuttings. The plant is reproduced asexually and asexually only.

A plant and flower of the new variety are shown in full color in the accompanying illustration.

A deailed description of the new variety follows, and to facilitate identification of the important colors, the color terminology adopted by the British Horticultural Color Charts has been followed. (Reference is to "Horticultural Color Charts" issued by the British Color Council in two volumes, in collaboration with the Royal Horticultural Society, copyright by Robert F. Wilson, published 1938–41.)

*The plant*

Parentage: Seedling resulting from open pollenation.
*Pollen parent.*—Unknown.
*Seed parent.*—Azalea "Laughing Waters," an unpatented variety.

Growth: The plant is of a moderately vigorous, compact, spreading habit of growth, well-clothed with foliage. The ultimate height of the plant is not known, but under normal conditions it should reach a height of about 2½ to 3½ feet, with a spread of approximately 5 to 6 feet.

Branches: New growth is a light green, gradually changing to light brown as the branch matures. The new growth is densely covered by white hairs that gradually change to brown as the branch matures.

Growth habit: Branching starts just above ground level, and has a tendency to be mounding.

Foliage: The leaves are of good substance and are semi-glossy.

Shape: The leaves are best described as being elliptic to oblanceolate. Margins are entire and ciliate. Apex of the leaf is mucronulate; base is attenuate. New leaves are Scheeles Green 860/1 on the upper surface and Scheeles Green 860/3 on the underside. Mature leaves are slightly darker than Spinach Green o960 on the upper surface and o960/2 on the underside. Both upper and bottom surfaces of leaves are remotely strigose hairy.

Size: Leaves are from 1⅝ to 3 inches in length, and from ⅝ to 1 inch in width. Petiole is from ¼ to ⅜ inch in length, and is hairy.

Arrangement: Leaves are alternate on the branches.

Veins: The midrib on the upperside and underside of the leaf blade is strigose hairy and is lighter in color than the leaf blade.

*The flower*

The plant sets an occasional bloom from October until late January, when it produces its heaviest bloom, lasting through February and into early March. It will then continue to produce an occasional bloom until late April.

Form: Flowers are of the single type, with an occasional flower being semi-double. Flowers have a natural spread of from 2¾ to 3 inches.

Petals: Petals are five in number, with the margins undulate.

Color: Basic color of the corolla tube and petal lobes is Solferino Purple 26/2. The standard petal and the two wing petals are blotched with Spiraea Red o25.

I claim:

A new and distinct variety of azalea plant, substantially as herein described and illustrated, and characterized particularly as to novelty by the unique coloring of its flowers, both in shade and in pattern; by its abundant, rich green foliage; by its ability to grow and flower in full sun or light shade; and by its compact, densely branched habit of growth.

No references cited.

ABRAHAM G. STONE, *Primary Examiner.*

ROBERT E. BAGWILL, *Examiner.*